United States Patent
Knight et al.

(10) Patent No.: US 11,090,095 B2
(45) Date of Patent: Aug. 17, 2021

(54) METHOD AND APPARATUS FOR AN ORTHOPEDIC FIXATION SYSTEM

(71) Applicant: BioMedical Enterprises, Inc., San Antonio, TX (US)

(72) Inventors: Adam T. Knight, San Antonio, TX (US); Daniel F. Cheney, San Antonio, TX (US); Eric A. Marcano, San Antonio, TX (US); David J. Pancratz, Helotes, TX (US)

(73) Assignee: BioMedical Enterprises, Inc., San Antonio, TX (US)

( * ) Notice: Subject to any disclaimer, the term of this patent is extended or adjusted under 35 U.S.C. 154(b) by 91 days.

(21) Appl. No.: 16/232,344

(22) Filed: Dec. 26, 2018

(65) Prior Publication Data

US 2019/0133662 A1 May 9, 2019

Related U.S. Application Data

(60) Continuation of application No. 14/033,785, filed on Sep. 23, 2013, now abandoned, which is a division of
(Continued)

(51) Int. Cl.
 *A61B 17/88* (2006.01)
 *A61L 2/26* (2006.01)
 (Continued)

(52) U.S. Cl.
 CPC .......... *A61B 17/88* (2013.01); *A61B 17/0642* (2013.01); *A61B 17/0682* (2013.01);
 (Continued)

(58) Field of Classification Search
 CPC . A61B 17/88; A61B 17/1775; A61B 17/0642; A61B 17/0682; A61B 19/26;
 (Continued)

(56) References Cited

U.S. PATENT DOCUMENTS

| 1,106,241 A | 8/1914 | Richardson |
| 2,544,492 A | 3/1947 | Downing |

(Continued)

FOREIGN PATENT DOCUMENTS

| EP | 0682920 B1 | 2/1995 |
| EP | 0857462 A1 | 1/1998 |

(Continued)

OTHER PUBLICATIONS

4-Fusion Shape Memory Implant Training Slide Images, Memometal, Inc., 2008.

(Continued)

*Primary Examiner* — Dariush Seif

(74) *Attorney, Agent, or Firm* — Christopher L. Makay

(57) ABSTRACT

An orthopedic fixation system includes a sterile packaged implant kit and a sterile packaged instrument kit. The sterile packaged implant kit includes at least one surgical implant, an insertion device, and an implant package adapted to receive the at least one surgical implant and the insertion device therein. The implant package maintains the at least one surgical implant and the insertion device sterile after sterilization of the sterile packaged implant kit. The sterile packaged instrument kit includes one or more instruments necessary to use the sterile packaged implant kit and an instrument package adapted to receive the one or more instruments therein. The instrument package maintains the one or more instruments sterile after sterilization of the sterile packaged instrument kit.

12 Claims, 18 Drawing Sheets

Related U.S. Application Data application No. 13/385,387, filed on Feb. 16, 2012, now Pat. No. 8,584,853.

(51) Int. Cl.

| | |
|---|---|
| *A61B 50/30* | (2016.01) |
| *A61B 90/00* | (2016.01) |
| *A61B 17/064* | (2006.01) |
| *A61B 17/068* | (2006.01) |
| *B65D 85/00* | (2006.01) |
| *A61B 17/17* | (2006.01) |
| *A61B 50/00* | (2016.01) |
| *A61B 50/33* | (2016.01) |
| *A61B 17/00* | (2006.01) |

(52) U.S. Cl.
CPC .............. *A61B 50/30* (2016.02); *A61B 90/06* (2016.02); *A61L 2/26* (2013.01); *B65D 85/00* (2013.01); *A61B 17/1775* (2016.11); *A61B 50/33* (2016.02); *A61B 2017/00867* (2013.01); *A61B 2050/006* (2016.02); *A61B 2050/3008* (2016.02); *A61B 2090/061* (2016.02); *A61L 2202/182* (2013.01)

(58) Field of Classification Search
CPC ... A61B 50/30; A61B 90/06; A61B 2050/006; A61B 2050/3008; A61B 50/33; A61B 2090/061; A61B 2017/00867; A61L 2/26; A61L 2202/182; B65D 85/00
USPC .................. 53/425; 606/916, 102–105, 300, 606/213–220
See application file for complete search history.

(56) References Cited

U.S. PATENT DOCUMENTS

| | | | |
|---|---|---|---|
| 2,593,546 A | 4/1952 | Dietsch | |
| 3,939,828 A | 2/1976 | Mohr et al. | |
| 3,960,147 A | 6/1976 | Murray | |
| 4,269,180 A | 5/1981 | Dall et al. | |
| 4,324,331 A | 4/1982 | Ignasiak | |
| 4,438,769 A | 3/1984 | Pratt et al. | |
| 4,444,181 A * | 4/1984 | Wevers | A61B 17/0642 606/75 |
| 4,485,816 A | 12/1984 | Krumme | |
| 4,526,174 A | 7/1985 | Froehlich | |
| 4,570,623 A | 2/1986 | Ellison et al. | |
| 4,592,346 A | 6/1986 | Jurgutis | |
| 4,608,972 A * | 9/1986 | Small | A61B 17/176 606/96 |
| 4,665,906 A | 5/1987 | Jervis | |
| 4,713,077 A * | 12/1987 | Small | A61B 17/176 128/898 |
| 4,723,540 A * | 2/1988 | Gilmer, Jr. | A61B 17/0642 411/456 |
| 4,730,726 A | 3/1988 | Holzwarth | |
| 4,869,243 A | 9/1989 | Huene | |
| 5,067,957 A | 11/1991 | Jervis | |
| 5,112,336 A * | 5/1992 | Krevolin | A61B 17/1778 606/87 |
| 5,163,557 A * | 11/1992 | Sokolowski | A61L 2/26 206/439 |
| 5,171,252 A | 12/1992 | Friedland | |
| 5,246,443 A | 9/1993 | Vlai | |
| D344,664 S * | 3/1994 | Malkinson | D8/85 |
| 5,357,732 A * | 10/1994 | Markle | A61B 5/145 53/410 |
| 5,425,489 A | 6/1995 | Shichman et al. | |
| 5,462,549 A * | 10/1995 | Glock | A61B 90/06 606/86 R |
| 5,474,557 A | 12/1995 | Mai | |
| 5,478,354 A | 12/1995 | Tovey et al. | |
| 5,769,856 A * | 6/1998 | Dong | A61F 2/4081 606/80 |
| 5,779,707 A | 7/1998 | Bertholet et al. | |
| 5,785,713 A | 7/1998 | Jobe | |
| 5,976,159 A | 11/1999 | Bolduc et al. | |
| 6,001,110 A | 12/1999 | Adams | |
| 6,187,009 B1 | 2/2001 | Herzog et al. | |
| 6,268,589 B1 | 7/2001 | Flot | |
| 6,323,461 B2 | 11/2001 | Flot | |
| 6,412,639 B1 | 7/2002 | Hickey | |
| 6,607,542 B1 | 8/2003 | Wild | |
| 6,632,224 B2 | 10/2003 | Cachia et al. | |
| 6,638,297 B1 | 10/2003 | Huitema | |
| 6,648,890 B2 | 11/2003 | Culbert et al. | |
| D486,051 S * | 2/2004 | Parry | D8/82 |
| 6,685,706 B2 | 2/2004 | Padget et al. | |
| 6,685,708 B2 | 2/2004 | Monassevitch et al. | |
| 6,783,531 B2 | 8/2004 | Allen | |
| 6,827,723 B2 * | 12/2004 | Carson | A61B 34/20 606/130 |
| 7,115,129 B2 | 10/2006 | Heggeness | |
| 7,240,677 B2 | 7/2007 | Fox | |
| 7,306,601 B2 | 12/2007 | McGrath et al. | |
| 7,344,539 B2 | 3/2008 | Serhan et al. | |
| 7,428,807 B2 * | 9/2008 | Vander Bush | A61M 5/002 206/432 |
| 7,556,647 B2 | 7/2009 | Drews et al. | |
| 7,678,115 B2 * | 3/2010 | D'Alessio, II | A61F 2/4684 606/88 |
| 7,857,851 B2 | 12/2010 | Zannis et al. | |
| 7,867,265 B2 | 1/2011 | Beutter | |
| 8,057,490 B2 | 11/2011 | Harris | |
| 8,079,468 B2 | 12/2011 | Pleil et al. | |
| D652,144 S * | 1/2012 | Stotland | D24/140 |
| 8,114,138 B2 * | 2/2012 | Nehls | A61B 17/7059 606/281 |
| 8,118,952 B2 | 2/2012 | Gall et al. | |
| 8,137,351 B2 | 3/2012 | Prandi | |
| 8,191,220 B2 | 6/2012 | Magnuson et al. | |
| 8,211,109 B2 | 7/2012 | Groiso | |
| D669,984 S * | 10/2012 | Cheney | D24/140 |
| D669,985 S * | 10/2012 | Cheney | D24/140 |
| 8,342,841 B2 | 1/2013 | Vogel et al. | |
| D676,962 S * | 2/2013 | Cheney | D24/145 |
| 8,393,517 B2 * | 3/2013 | Milo | A61B 17/0684 227/181.1 |
| 8,584,853 B2 * | 11/2013 | Knight | A61L 2/26 206/439 |
| 8,596,514 B2 | 12/2013 | Miller et al. | |
| 8,685,068 B2 | 4/2014 | Sixto et al. | |
| 9,101,349 B2 * | 8/2015 | Knight | B65D 85/00 |
| D780,312 S * | 2/2017 | Perkins | D24/155 |
| 9,585,656 B2 | 3/2017 | Taber et al. | |
| D799,042 S * | 10/2017 | Perkins | D24/155 |
| 9,855,036 B2 | 1/2018 | Palmer et al. | |
| 9,931,115 B2 | 4/2018 | Morgan et al. | |
| 9,931,740 B2 * | 4/2018 | Clifford | B25B 23/0035 |
| 2002/0050463 A1 | 5/2002 | McDowell | |
| 2002/0112981 A1 | 8/2002 | Cooper et al. | |
| 2004/0097970 A1 | 5/2004 | Hughett | |
| 2004/0106925 A1 | 6/2004 | Culbert | |
| 2004/0204716 A1 * | 10/2004 | Fanger | A61B 17/1728 606/96 |
| 2005/0033430 A1 * | 2/2005 | Powers | A61B 50/33 623/17.11 |
| 2005/0043757 A1 | 2/2005 | Arad et al. | |
| 2005/0080454 A1 | 4/2005 | Drews et al. | |
| 2005/0009660 A1 | 5/2005 | Allen | |
| 2005/0107807 A1 | 5/2005 | Nakao | |
| 2005/0113832 A1 * | 5/2005 | Molz, IV | A61B 17/0642 606/86 A |
| 2005/0143749 A1 | 6/2005 | Zalenski et al. | |
| 2005/0273114 A1 * | 12/2005 | Novak | A61B 17/15 606/88 |
| 2006/0064108 A1 * | 3/2006 | Blaylock | A61B 90/06 606/102 |
| 2006/0106388 A1 * | 5/2006 | Lococo | A61C 1/084 623/16.11 |

(56) References Cited

U.S. PATENT DOCUMENTS

| | | | |
|---|---|---|---|
| 2006/0167459 A1* | 7/2006 | Groiso | A61B 17/0642 606/248 |
| 2006/0229627 A1* | 10/2006 | Hunt | A61F 2/4465 606/86 R |
| 2007/0118141 A1* | 5/2007 | Marchyn | A61B 17/1677 606/88 |
| 2007/0118224 A1* | 5/2007 | Shah | A61F 2/4611 623/17.15 |
| 2008/0015599 A1* | 1/2008 | D'Alessio | A61B 17/155 606/79 |
| 2008/0065153 A1 | 3/2008 | Allard et al. | |
| 2008/0110957 A1 | 5/2008 | McBride et al. | |
| 2008/0132894 A1* | 6/2008 | Coilard-Lavirotte | A61B 17/1604 606/60 |
| 2008/0195099 A1* | 8/2008 | Minas | A61B 17/152 606/70 |
| 2008/0306480 A1* | 12/2008 | Wilson | A61B 17/1782 606/60 |
| 2008/0319443 A1* | 12/2008 | Focht | A61B 17/0642 606/75 |
| 2009/0048675 A1* | 2/2009 | Bhatnagar | A61B 17/864 623/17.16 |
| 2009/0062800 A1 | 3/2009 | Shano | |
| 2009/0062806 A1* | 3/2009 | Scott | A61B 17/1764 606/84 |
| 2009/0105761 A1* | 4/2009 | Robie | A61B 17/7067 606/246 |
| 2009/0216285 A1* | 8/2009 | Ek | A61F 2/4657 606/86 R |
| 2009/0254090 A1* | 10/2009 | Lizee | A61B 17/0642 606/75 |
| 2009/0272786 A1 | 11/2009 | Zeiner et al. | |
| 2010/0004657 A1* | 1/2010 | Dudasik | A61B 17/1757 606/96 |
| 2010/0125301 A1* | 5/2010 | Kinmon | A61B 17/1757 606/300 |
| 2010/0133316 A1* | 6/2010 | Lizee | A61B 17/0642 227/175.1 |
| 2010/0191258 A1 | 7/2010 | Harris et al. | |
| 2010/0217270 A1* | 8/2010 | Polinski | A61F 2/0095 606/87 |
| 2010/0237128 A1* | 9/2010 | Miller | A61B 17/0642 227/175.1 |
| 2011/0093018 A1* | 4/2011 | Prasad | A61B 17/8014 606/282 |
| 2011/0155592 A1 | 6/2011 | Liccardo et al. | |
| 2011/0186456 A1* | 8/2011 | Bertazzoni | A61B 17/154 206/438 |
| 2011/0270327 A1* | 11/2011 | Blakemore | A61B 17/1764 606/86 R |
| 2012/0024937 A1 | 2/2012 | Allen | |
| 2012/0085809 A1* | 4/2012 | Milo | A61B 17/0644 227/181.1 |
| 2012/0209305 A1 | 8/2012 | Deodhar et al. | |
| 2012/0209401 A1 | 8/2012 | Euteneuer et al. | |
| 2012/0228355 A1* | 9/2012 | Combrowski | A61B 17/1285 227/175.1 |
| 2012/0259419 A1* | 10/2012 | Brown | A61F 2/4225 623/21.19 |
| 2012/0305427 A1 | 12/2012 | Felder et al. | |
| 2013/0026206 A1* | 1/2013 | Fox | A61B 17/0682 227/176.1 |
| 2013/0026207 A1 | 1/2013 | Fox | |
| 2013/0030437 A1 | 1/2013 | Fox | |
| 2013/0030438 A1* | 1/2013 | Fox | A61B 17/0682 606/75 |
| 2013/0184476 A1 | 7/2013 | McIff et al. | |
| 2013/0231667 A1 | 9/2013 | Taylor et al. | |
| 2014/0018809 A1* | 1/2014 | Allen | A61B 17/8004 606/75 |
| 2014/0020333 A1* | 1/2014 | Knight | A61B 17/0682 53/425 |
| 2014/0058446 A1* | 2/2014 | Bernstein | A61B 17/7059 606/246 |
| 2014/0097228 A1* | 4/2014 | Taylor | A61B 17/0682 227/181.1 |
| 2014/0175157 A1 | 6/2014 | Vold et al. | |
| 2014/0276830 A1 | 9/2014 | Cheney | |
| 2014/0277516 A1 | 9/2014 | Miller et al. | |
| 2014/0358187 A1* | 12/2014 | Taber | A61B 17/0682 606/86 R |
| 2015/0133940 A1* | 5/2015 | Palmer | A61B 17/7266 606/75 |
| 2015/0238238 A1* | 8/2015 | Cheney | A61B 17/1728 606/281 |
| 2015/0257801 A1 | 9/2015 | Palmer et al. | |
| 2016/0015384 A1 | 1/2016 | Roedl et al. | |
| 2016/0066907 A1 | 3/2016 | Cheney et al. | |
| 2016/0074037 A1 | 3/2016 | Cheney et al. | |
| 2016/0235460 A1* | 8/2016 | Wahl | A61B 17/0682 |
| 2017/0000482 A1* | 1/2017 | Averous | A61B 17/0642 |
| 2017/0065275 A1 | 3/2017 | Cheney | |
| 2017/0281157 A1 | 10/2017 | Hartdegen et al. | |
| 2020/0100820 A1* | 4/2020 | Hollis | A61B 17/846 |

FOREIGN PATENT DOCUMENTS

| | | |
|---|---|---|
| EP | 0826340 A2 | 3/1998 |
| EP | 1870042 A1 | 12/2007 |
| FR | 2874166 A1 | 2/2006 |
| WO | 1992017122 A2 | 10/1992 |
| WO | 2008129061 A1 | 10/2008 |
| WO | 2013055824 A1 | 4/2013 |

OTHER PUBLICATIONS

4-Fusion Shape Memory Implant Brochure, Memometal, Inc., Jun. 23, 2009.

MemoGraph Brochure, M.B.A. (Memory Biological Application), Parc Club de Nancy de Brabois,Batiment B11, 4 allee Vincennes, 54500 Vandceurve, France, 1999.

OSStaple Brochure Including pictures of staple loaded in shipping block, BioMedical Enterprises, Inc., 14875 Omicron Drive, Suite 205, San Antonio, TX 78245, 2010.

E. A. Van Amerongen et al., "Four-Corner Arthrodesis Using the Quad Memory Staple," Journal of Hand Surgery (European vol. 2008) (Jan. 7, 2009).

U. Rethnam et al., "Mechanical Characteristics of Three Staples Commonly Used in Foot Surgery," Journal of Foot and Ankle Research (Feb. 25, 2009) available at http://www.jfootankleres.com/content/2/1/5.

T. F. Smith, "The Bone Staple: Tried and True Superhero of Bone Fixation," Educational Materials Update Chapter 41 (2010) available at www.podiatryinstitute.com/pdfs/Update 2010/2010 41.pdf.

ELEVEST Procedure Kit, Instructions for Use by CooperSurgical (© 2007).

Agee WristJack, Surgeon's Manual by Hand BioMechanics Labs, Inc. (© 1990-2002).

Development of a Nickel-Titanium Shape Memory Alloy Bone Repair Staple and Other In-Vivo Orthopaedic and Cardio-Vascular Devices, A.W. Anson, D.H.R. Jenkins, and S. Andrews, Proceedings of the Technology Transfer Workshop, Held at ESA/ESTEC Noordwijk, The Netherlands, May 1994 (ESA SP-364, Aug. 1994).

Superelastic Fixation System Brochure, Memometal Inc., USA, Aug. 12, 2009.

Shape Memory Staple System for Arthrodesis and Skeletal Fixation of the Hand Brochure, Core Essence Orhtopaedics, Inc., 2009.

ENTact™ Septal Stapler, Product brochure by ENTrigue Surgical, Inc. (© 2009).

R. M. Sloan et al., "Orthopedic Fixation Devices," Radiographics at 823 (Sep. 1991).

J. Arthur, "Improving Operating Efficiency in Five Days," Lean Six Sigma for Hospitals, McGraw-Hill (2011).

(56) References Cited

OTHER PUBLICATIONS

K. Yamauchi et al. (ed.), "Shape Memory and Superelastic Alloys: Applications and Technologies" (2011).
BioResearch Innovations (BRI), "Memodyn Compression Staple," FDA 510(K) disclosure (Jan. 2004).
G. C. Taylor et al., "Complications of Internal Fixation," Podiatry Institute Educational Materials Update Chapter 79 (1992).
Wright Medical Technology, Inc., "Charlotte Compression Staple as described by Robert Anderson, MD; Bruce Cohen, MD; and W. Hodges Davis, MD" (2007).
A. A. Weinbroum et al., "Efficiency of the Operating Room Suite," American Journal of Surgery 244-250 (2003).
G. G. Porto, "Safety by Design: Ten Lessons From Human Factors Research," Journal of Healthcare Risk Management 43-50 (Fall 2011).
Russell, Scott M., Design Considerations for Nitinol Bone Staples, Journals of Materials Engineering and Performance, vol. 18(5-6), Aug. 2009, USA.

\* cited by examiner

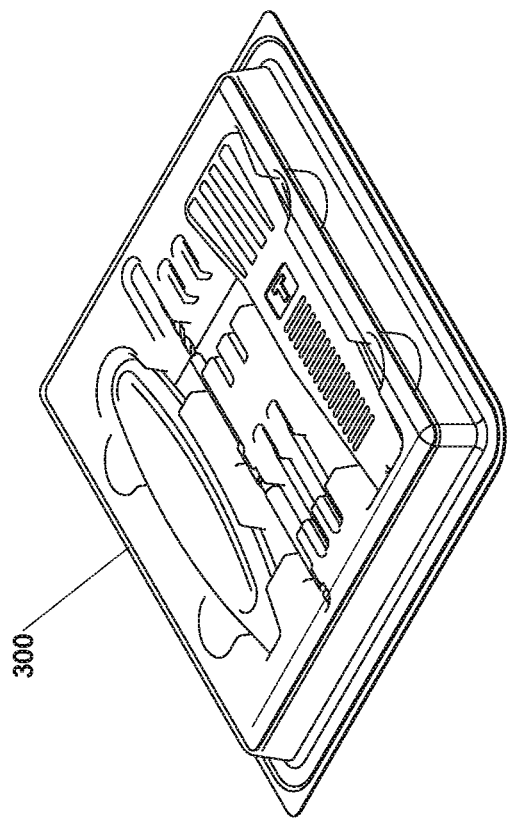
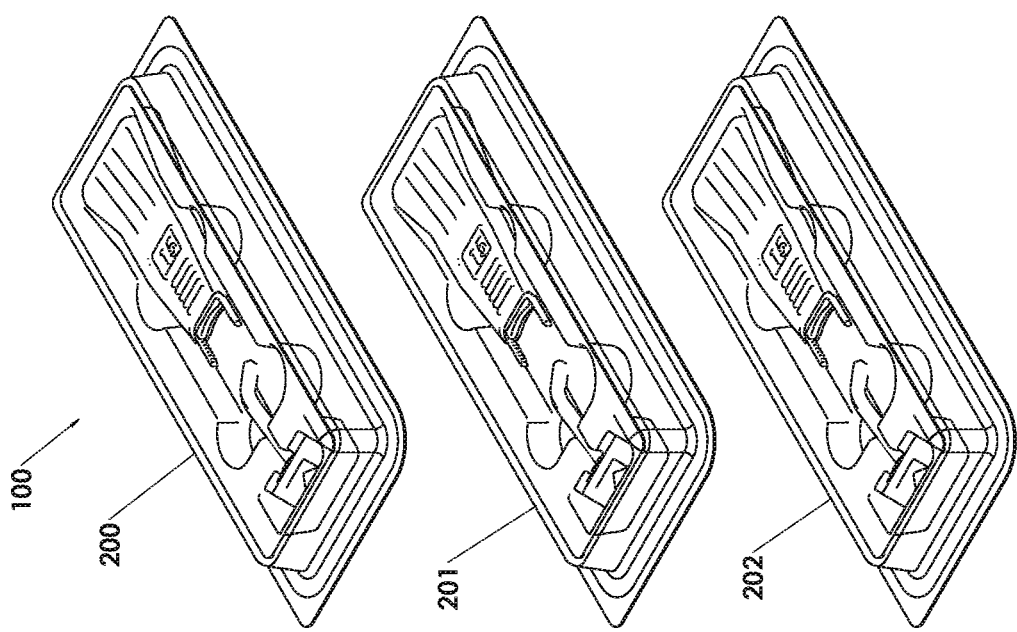
Figure 1A

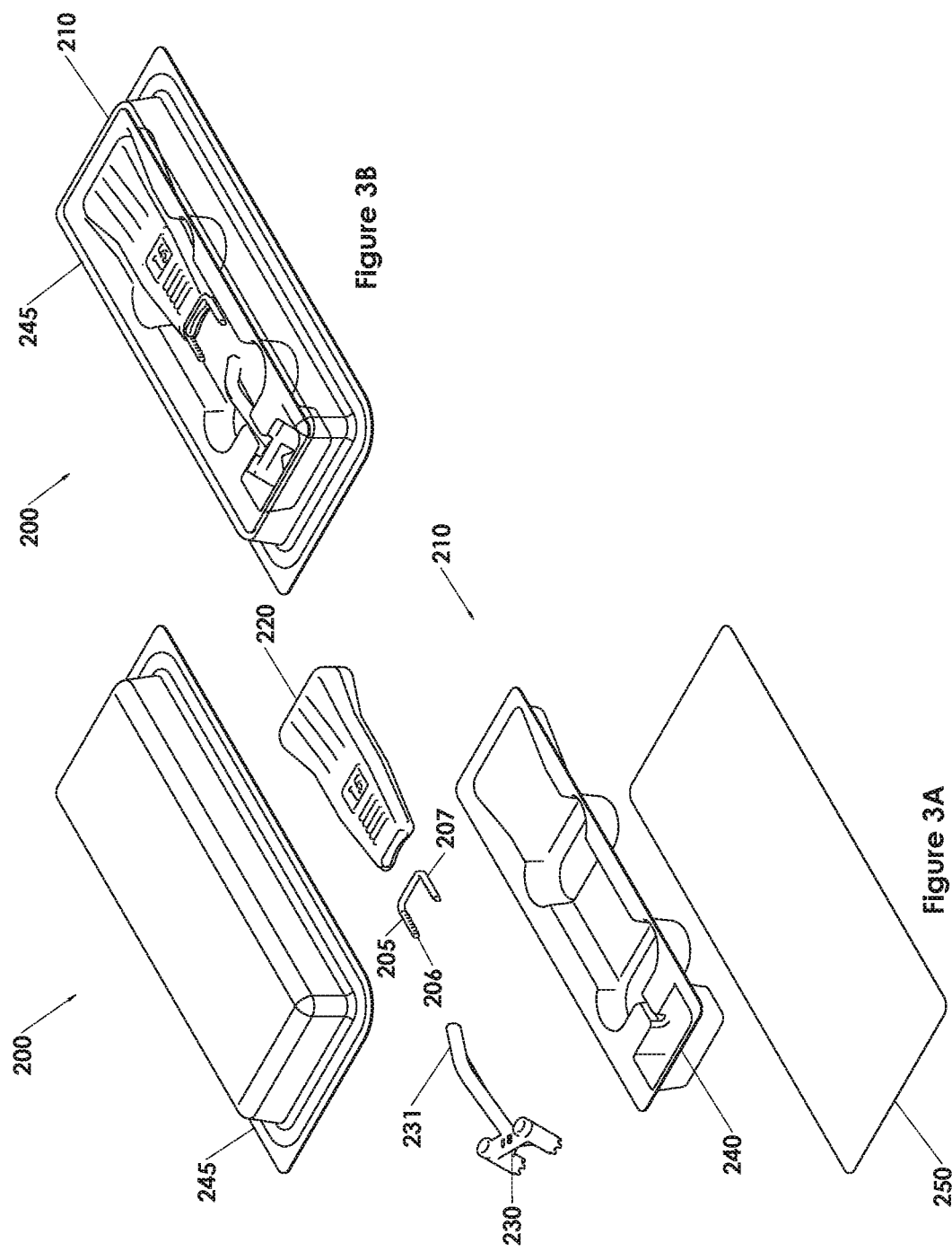

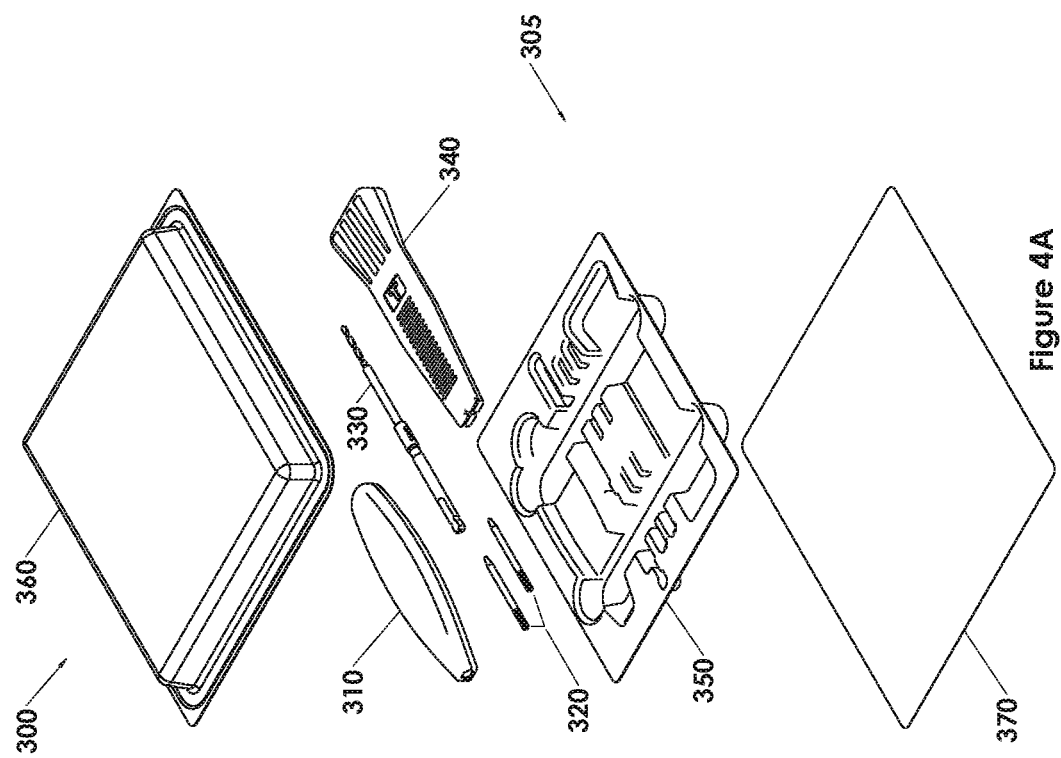

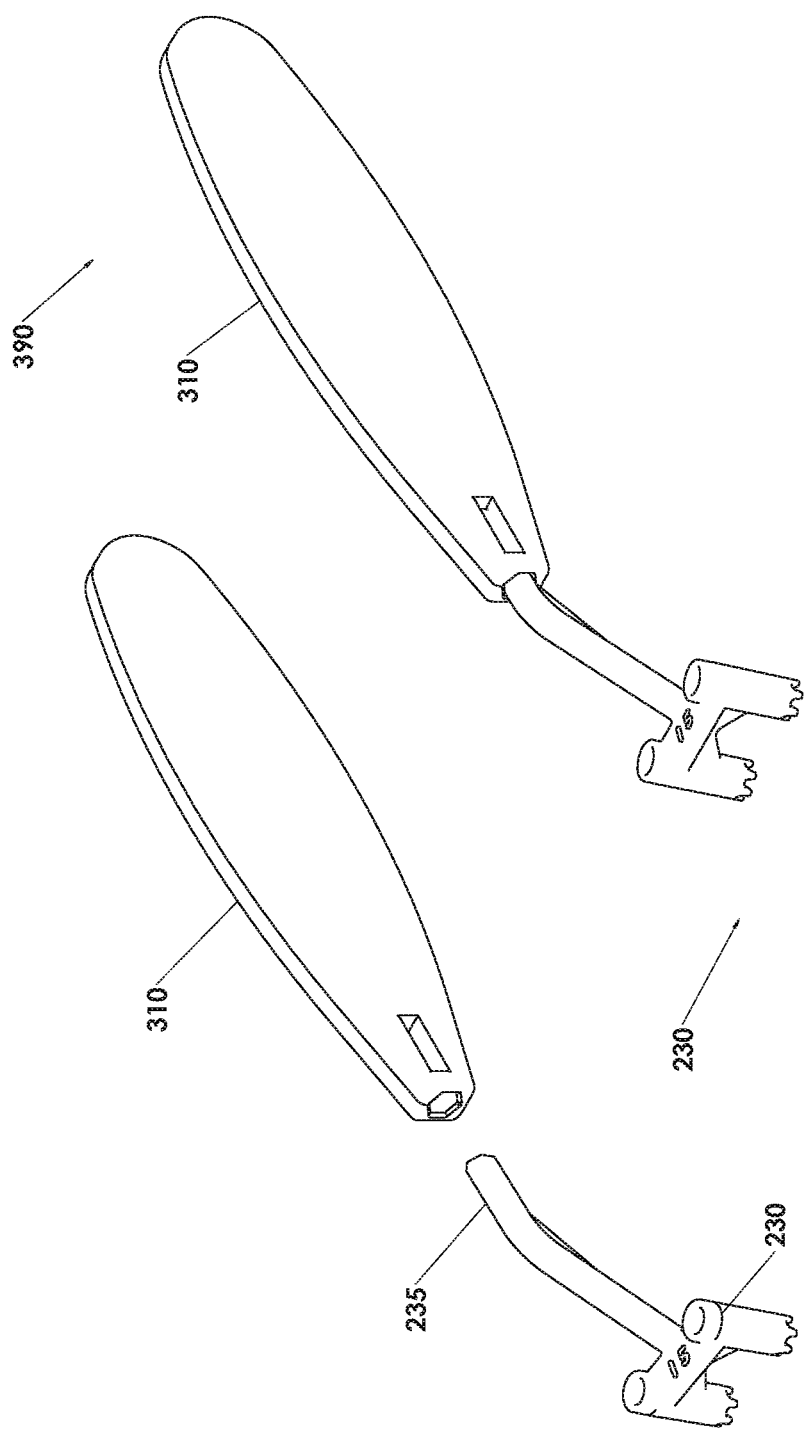

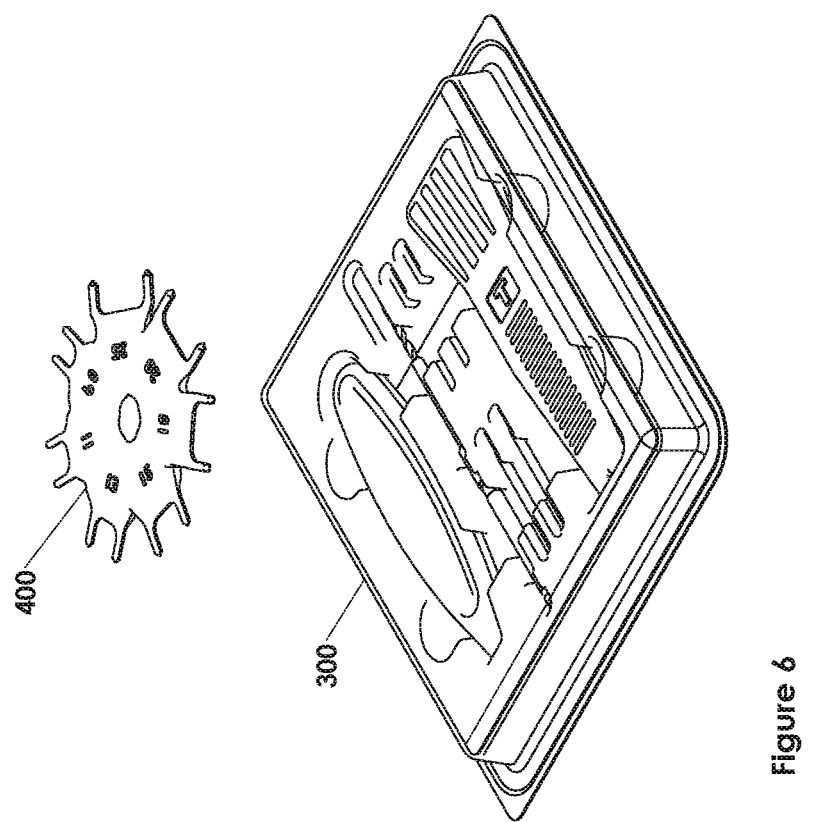
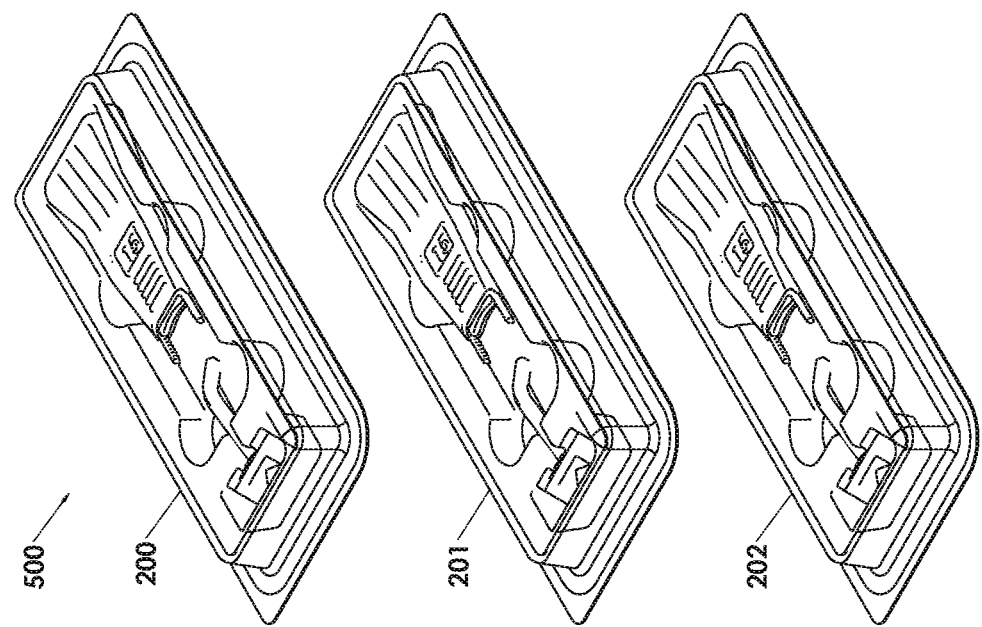
Figure 6

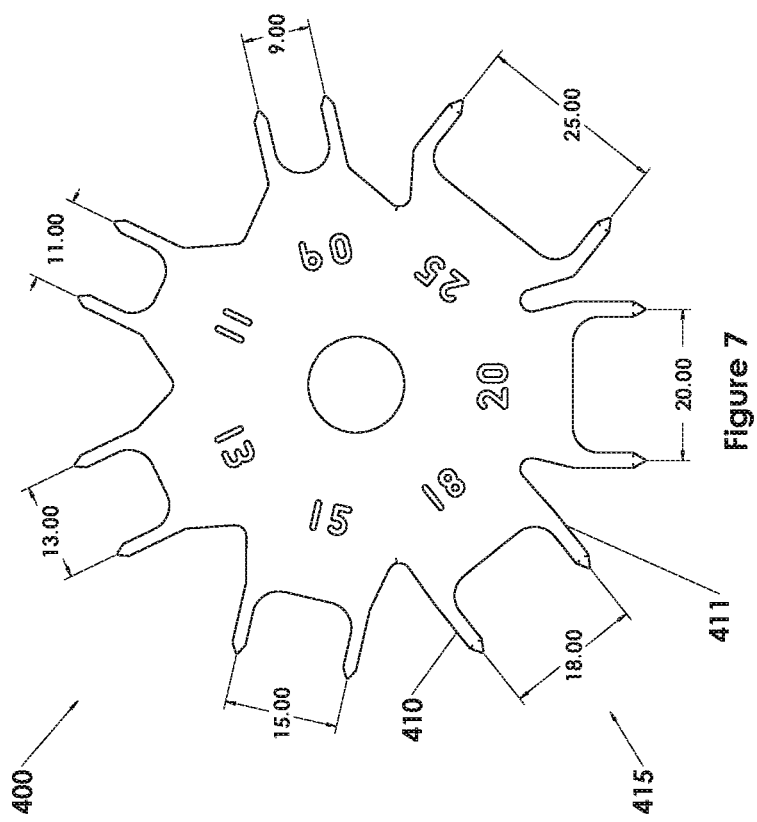

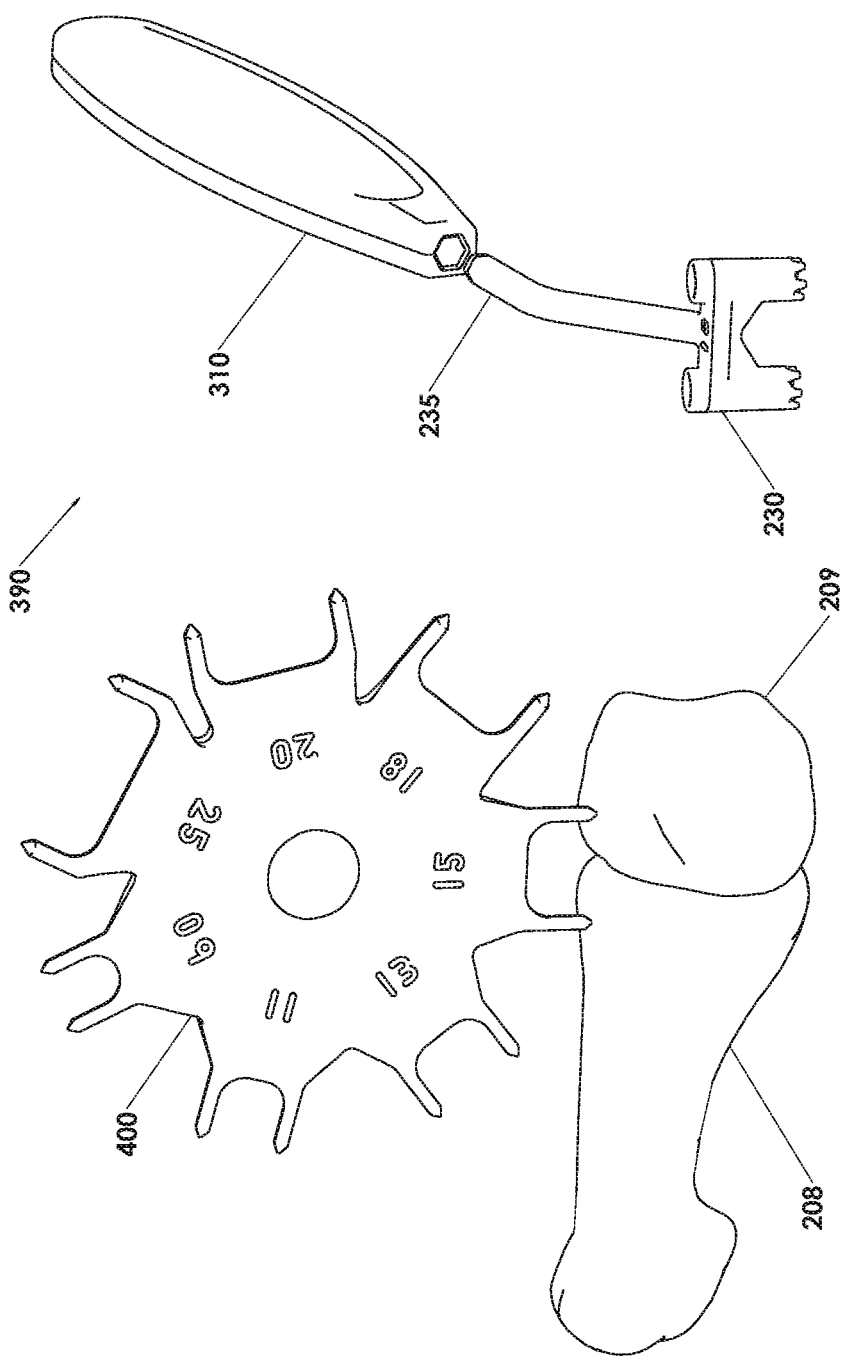

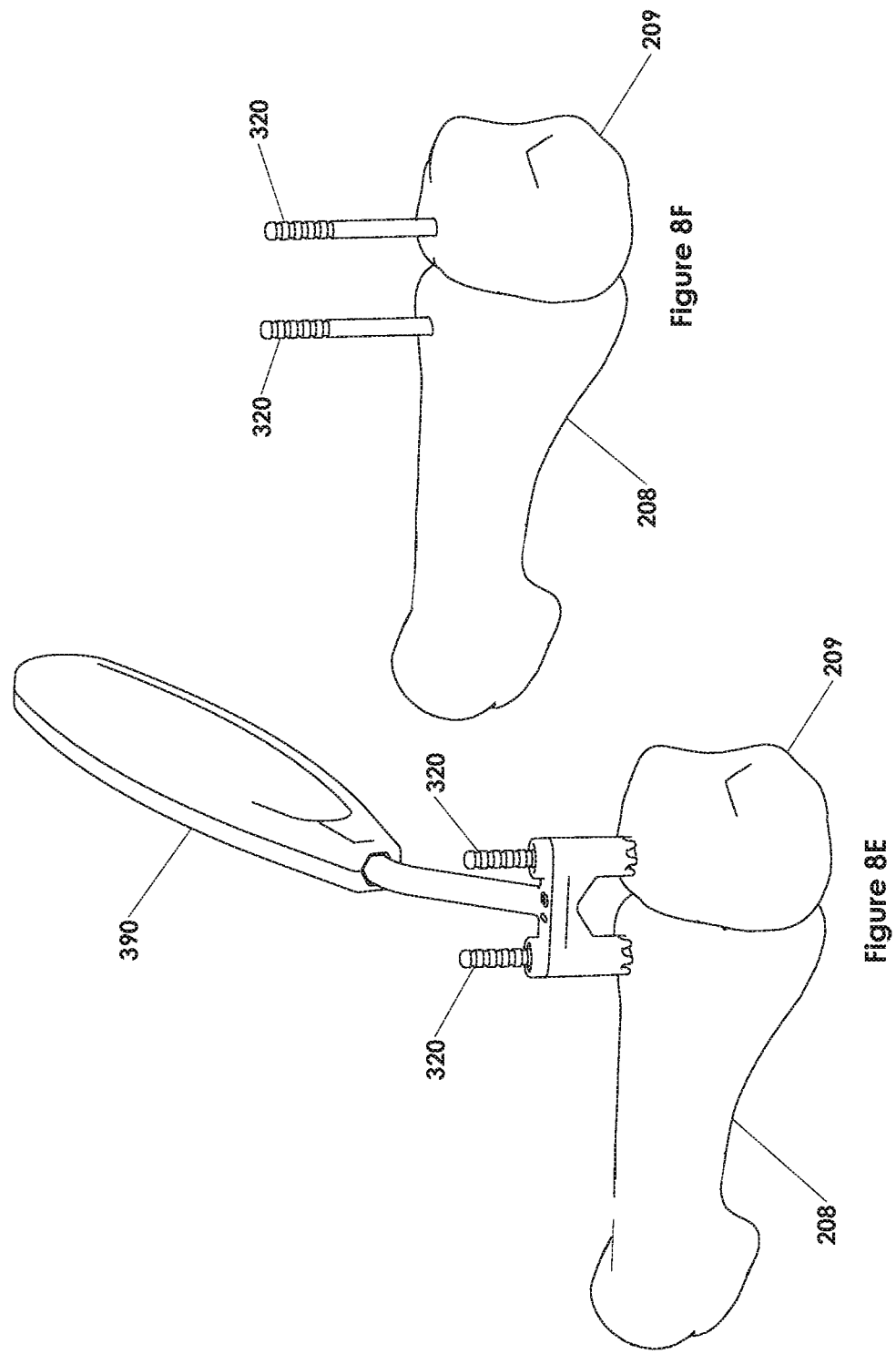

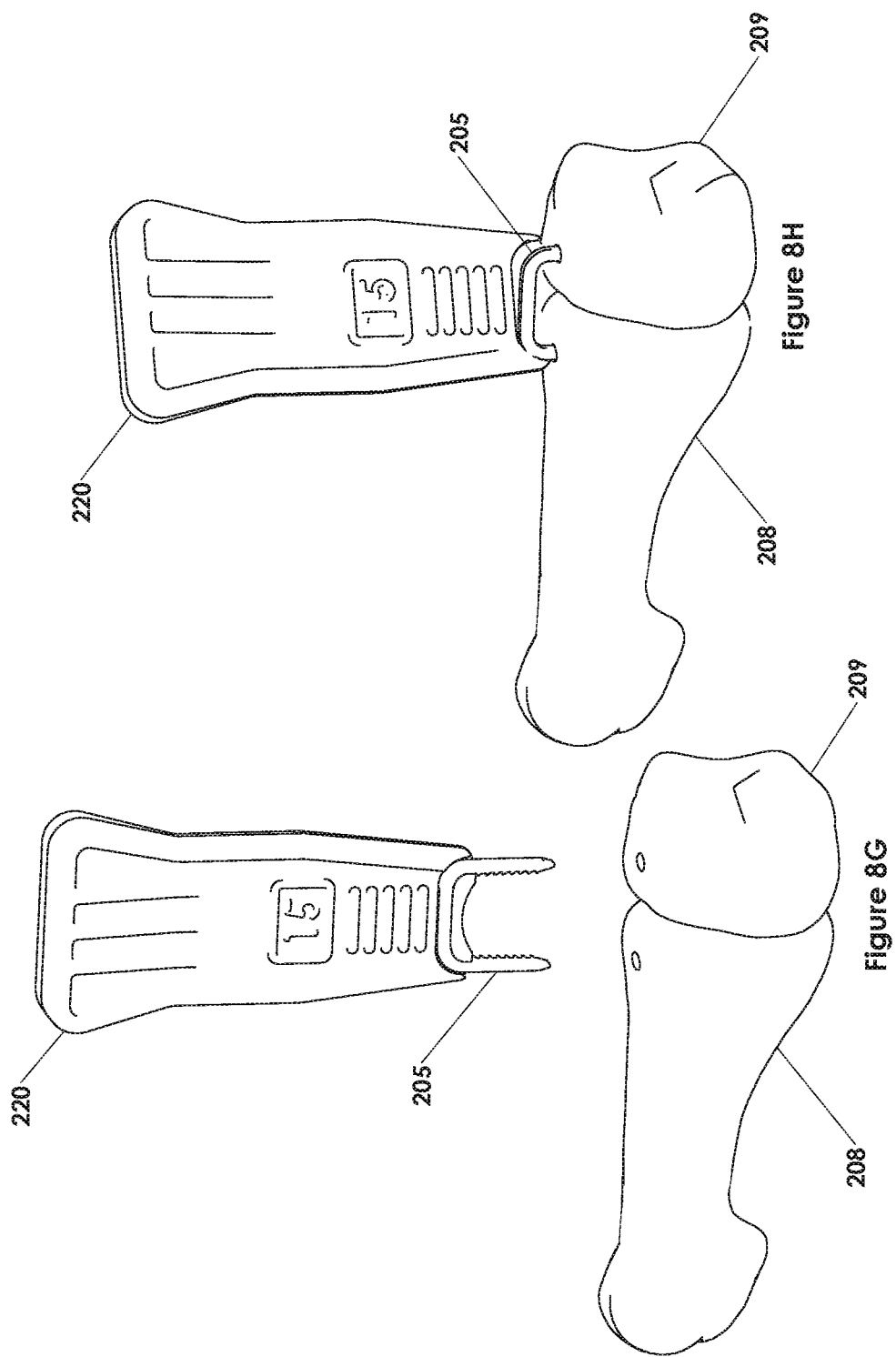

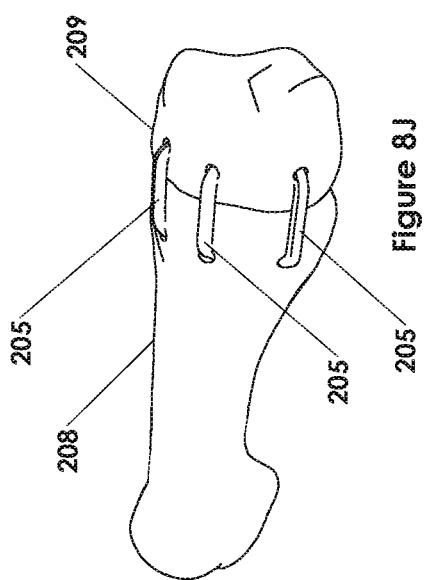
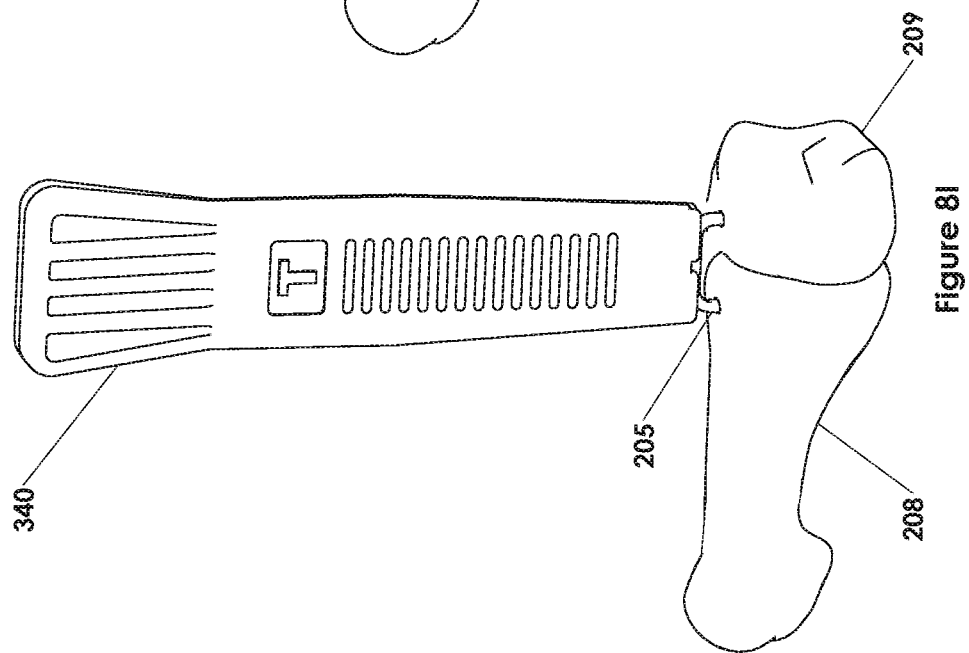

METHOD AND APPARATUS FOR AN ORTHOPEDIC FIXATION SYSTEM

BACKGROUND OF THE INVENTION

1. Field of the Invention

The present invention relates to an orthopedic fixation system consisting of a sterile packaged implant kit and a sterile packaged instrument kit.

2. Description of the Related Art

Bone fusion and healing in orthopedics often involves metallic implants being attached to bones in some way to fixate them together during the healing process. There are many forms of bone fixation devices including intramedullary devices, pins, screws, plates, and staples. Implants made from shape memory materials, such as nitinol, are a popular material for fixation because their shape memory and superelastic properties allow the device to create compression that can augment healing.

Many orthopedic implants are delivered to hospitals in a non-sterile form, and sterilized prior to surgery at the hospital. This is easier for the medical device manufacturer, since the implant requires less preparation than one that is sterile-packaged, however it places an onus on the hospital to insure sterility at the time of surgery. Frequently these implants are delivered in caddies, and the implants that are not used in surgery have to be re-sterilized before any subsequent surgical procedure.

Many other orthopedic implants are delivered to hospitals in a sterile packaged form. While this is more difficult and expensive for the medical device manufacturer, it is easier for the hospital to simply provide the implant at the time of surgery.

Finally, orthopedic instruments are generally provided as part of an instrument tray. The tray needs to be sterilized prior to surgical use. Furthermore, after surgery the tray needs to be properly cleaned, and then subsequently re-sterilized prior to the next use.

While there are numerous combinations of sterile and non-sterile orthopedic implants on the market, they all use an instrument tray that requires cleaning and sterilization.

The process of cleaning and sterilization at hospitals is known in the literature to periodically result in a phenomenon known as Hospital Acquired Infection. In this situation, patients are exposed to an infectious agent due to improperly cleaned or improperly sterilized equipment. Preventing and treating these infections is costly to hospitals.

Accordingly, a system is described herein for providing a sterile packaged implant kit mounted on an insertion device, and a complementary sterile packaged instrument kit. Methods of packaging the system, and delivering and using the system, are also presented.

SUMMARY OF THE INVENTION

The invention herein consists of a sterile packaged implant kit and a complementary sterile packaged instrument kit and methods for use and packaging thereof.

The sterile packaged implant kit includes an implant mounted on an insertion device and a drill guide. The sterile packaged implant kit further includes an implant tray shaped to hold the at least one surgical implant, the insertion device, and the drill guide therein, an implant outer cover insertable over the implant tray, and an implant seal securable over the implant outer cover. The implant seal encloses the implant outer cover such that the implant, the insertion device, and the drill guide remain sterile within the implant tray and implant outer cover after sterilization of the sterile packaged implant kit.

The sterile packaged instrument kit includes a drill bit, locating pins, an instrument handle, and an implant tamp. The sterile packaged instrument kit includes an instrument tray shaped to hold the drill bit, locating pins, instrument handle, and implant tamp therein, an instrument outer cover insertable over the instrument tray, and an instrument seal securable over the instrument outer cover. The instrument seal encloses the instrument outer cover such that the drill bit, locating pins, instrument handle, and implant tamp remain sterile within the instrument tray and instrument outer cover after sterilization of the sterile packaged instrument kit.

A method of using an orthopedic fixation system is as follows. A sterile packaged implant kit is opened to access an implant, insertion device, and drill guide. A sterile packaged instrument kit is opened to access a drill bit and tamp. The drill guide and the drill bit are used to drill holes in bone. The insertion device is used to insert the implant. The insertion device is also used to release and activate the implant. The tamp is used to push the implant flush with bone. The foregoing method may also include the use of a sizing wheel to determine the proper implant selection.

A method of packaging an orthopedic fixation system is as follows. An implant is inserted into an insertion device, and the insertion device is inserted into an implant tray. A drill guide is inserted into the implant tray. The implant tray is enclosed by inserting an implant outer cover over the implant tray and securing an implant seal over the implant outer cover. A drill bit is inserted into an instrument tray. An implant tamp is inserted into the instrument tray. One or more locating pins are inserted into the instrument tray. An instrument handle is inserted into the instrument tray. The instrument tray is enclosed by inserting an instrument outer cover over the instrument tray and securing an instrument seal over the instrument outer cover. The enclosed implant tray and the implant, the insertion device, and the drill guide therein are sterilized. The enclosed instrument tray and the drill bit, the implant tamp, the one or more locating pins, and the instrument handle therein are sterilized.

It is an object of the present invention to present the surgeon with an implant ready for implantation, pre-mounted on an insertion device.

It is a further object of the present invention to provide the implant and insertion in a sterile packaged format.

It is still further an object of the present invention to provide all the instruments needed for use with this implant in sterile packaged format.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

BRIEF DESCRIPTION OF THE DRAWINGS

FIG. 1A provides an isometric view of an orthopedic fixation system.

FIG. 3A provides an exploded isometric view of a sterile-packaged implant kit.

FIG. 3B provides an assembled isometric view of a sterile-packaged implant kit.

FIG. 4A provides an exploded isometric view of a sterile-packaged instrument kit.

FIG. 5A provides an exploded view of a drill guide and an instrument handle.

FIG. 5B provides an assembled isometric view of a drill guide system.

FIG. 6 provides an alternative embodiment of an orthopedic fixation system that includes a sizing guide.

FIG. 7 provides a plan view of a sizing guide.

FIGS. 8A-8J provide a sequence of images showing the use of an orthopedic fixation system.

DETAILED DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. It is further to be understood that the figures are not necessarily to scale, and some features may be exaggerated to show details of particular components or steps.

Figure 1B:
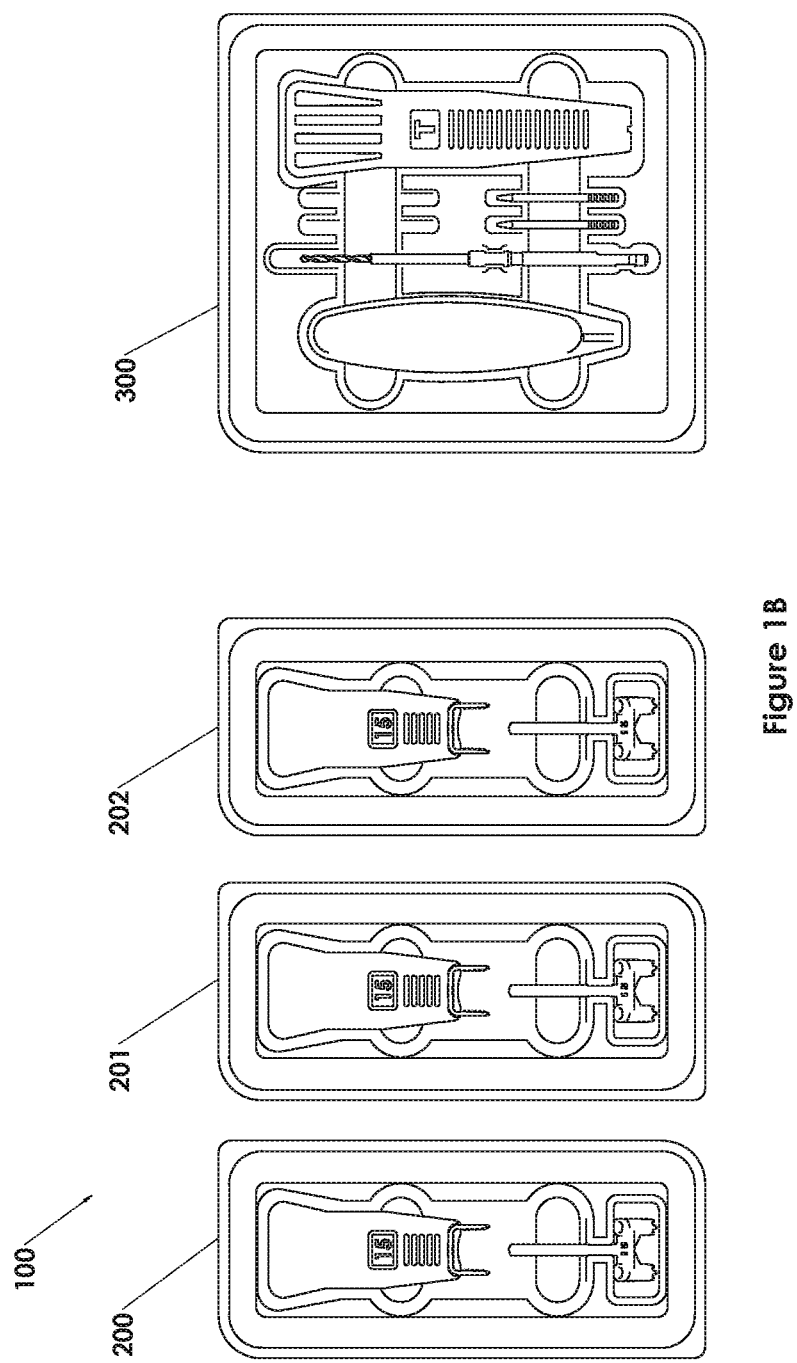
FIG. 1B provides a plan view of an orthopedic fixation system.

In this invention, a method and system for a sterile packaged implant and complementary sterile packaged instrument kit are described. As shown in FIGS. 1A and 1B, an orthopedic fixation system 100 consists of one or more sterile packaged implant kits 200, 201, and 202, and a sterile packaged instrument kit 300. Implant kits 200, 201, and 202 are identical, except that the implants may be sized differently as required by the physician.

Figure 2A:
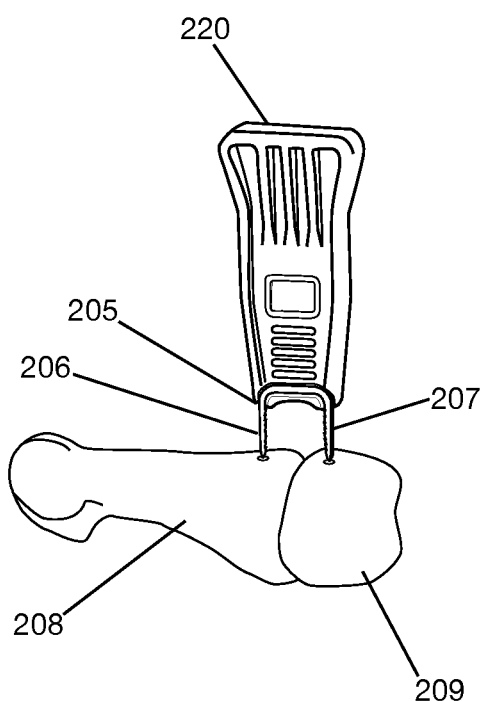
FIG. 2A provides an isometric view of an insertion device being used to insert an implant into bones.
Figure 2B:
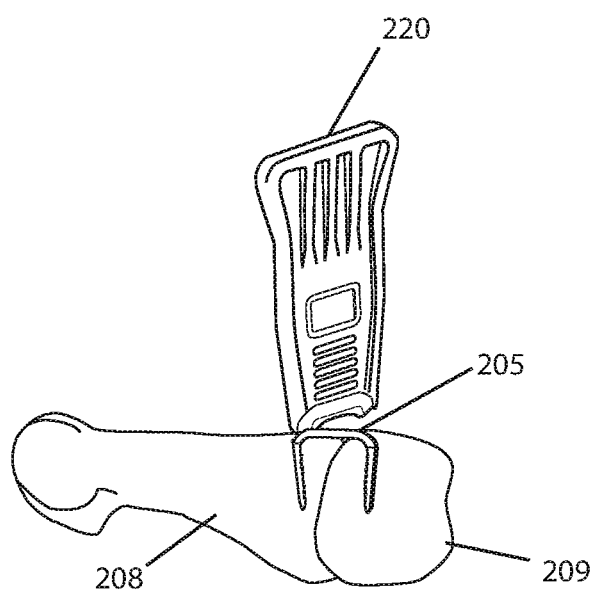
FIG. 2B provides an isometric view of an implant being released from an insertion stick into bones.

The orthopedic fixation implant is shown in FIG. 2A. The fixation implant 205 consists of an implant made from a shape-memory or superelastic material such as nitinol. Implant 205 has two legs, 206 and 207, that are designed to swing inward. Implant 205 is mounted on disposable insertion device 220. The insertion device 220 holds the implant 205 such that implants legs 206 and 207 are held mechanically in a parallel position for easier insertion into bone. FIG. 2A shows the implant 205 being inserted into two bones 208 and 209. Insertion device 220 can be twisted off implant 205, as shown in FIG. 2B, releasing the implant to squeeze bones 208 and 209.

The representative sterile packaged implant kit 200 is shown in more detail in exploded view FIG. 3A and assembly FIG. 3B. Implant kit 200 includes the aforementioned implant 205 and insertion device 220. Implant kit 200 also includes a drill guide 230. The purpose of drill guide 230 is to allow a surgeon to drill parallel holes into bone with the proper separation distance to match implant 205 and parallel legs 206 and 207. Drill guide 230 has a universal mating shaft 231 that can be used to attach to a handle. The entire assembly, consisting of implant 205 mounted to insertion device 220 and matching drill guide 230 are placed into an implant package 210 suitable to house implant 205, insertion device 220, and matching drill guide 230 and maintain implant 205, insertion device 220, and matching drill guide 230 sterile. In particular, implant 205, insertion device 220, and matching drill guide 230 are placed into an implant tray 240. Implant tray 240 could be made from thermoformed plastic or a similar material, and is shaped to hold and secure insertion device 220 and drill guide 230. While implant tray 240 in the preferred embodiment is shaped to hold insertion device 220 with implant 205 mounted, one of ordinary skill in the art will recognize that implant tray 240 could hold insertion device 220 and implant 205 separately. Implant tray 240 fits into implant outer cover 245, which protects all of the contents. Both implant tray 240 and implant outer cover 245 can be made from transparent plastic so that implant 205 is visible from outside. An implant seal 250 secures over and encloses implant outer cover 245 using any suitable means such as a heat and pressure activated adhesive. Implant seal 250 is made from a suitable material for insuring sterility while still allowing air passage. After sealing the system with implant seal 250, implant kit 200 can be sterilized by any common sterilization method such as gas, radiation, or another type. All of the components of implant kit 200 can be made from disposable materials such as injection molded plastic, metal, or other suitable materials, with the exception of implant 205 which is made from a superelastic or shape-memory material. It is an objective of implant kit 200 to be packaged and then sterilized to simplify the surgical implantation of implant 205, and then allow all of the other components to be discarded after surgery.

Figure 4B:
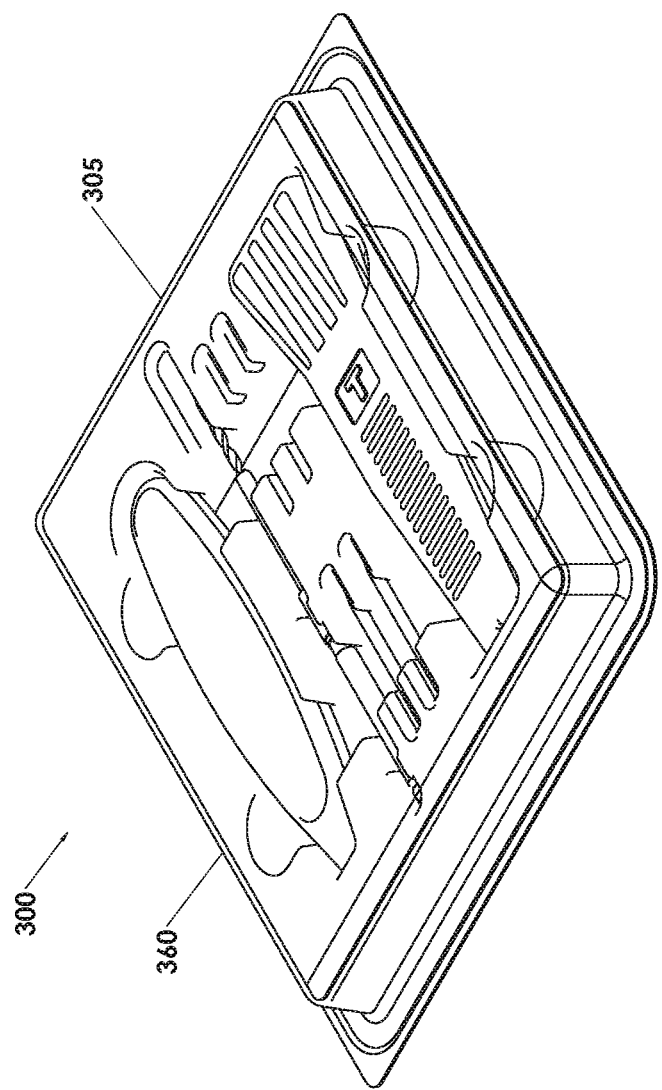
FIG. 4B provides an assembled isometric view of a sterile-packaged instrument kit.

Instrument kit 300 is displayed in exploded view FIG. 4A and assembly FIG. 4B. Instrument kit 300 is sterile-packaged and designed to work in conjunction with one or more implant kits 200, 201, or 202, or any combination of implant kits. In this embodiment, the instrument kit 300 includes multiple instruments needed by the surgeon for the implant kit. Instrument kit 300 consists of a handle 310 that mates with previously mentioned drill guide 230. Instrument kit 300 also consists of one or more locating pins 320, drill bit 330, and tamp 340. Locating pins 320 are used to fit inside drill guide 230. Drill bit 330 also fits inside drill guide 230 and can drill a hole in bone. Tamp 340 is used to press down on implant 205 to push it flush to bone. The handle 310, one or more locating pins 320, drill bit 330, and tamp 340 all fit into instrument package 305 suitable to house handle 310, one or more locating pins 320, drill bit 330, and tamp 340 and maintain handle 310, one or more locating pins 320, drill bit 330, and tamp 340 sterile. In particular, the handle 310, one or more locating pins 320, drill bit 330, and tamp 340 all fit into instrument tray 350. Instrument tray 350 is made from a thermoformed plastic or similar material that is shaped to conform and hold each instrument; namely, handle 310, one or more locating pins 320, drill bit 330, and tamp 340. Instrument tray 350 fits inside instrument outer cover 360. Both instrument tray 350 and instrument outer cover 360 can be made from transparent plastic so that each instrument is visible from outside. An instrument seal 370 secures over and encloses instrument outer cover 360 using any suitable means such as a heat and pressure activated adhesive. Instrument seal 370 is made from a suitable material for insuring sterility while still allowing air passage. Instrument seal 370 adheres to instrument outer tray 360 to allow instruments 310, 320, 330, and 340 to be sterilized and then maintain sterility. Instrument kit 300 is sterilized by any common method of sterilization such as gas or radiation.

FIG. 5A shows handle 310 and drill guide 230 being positioned for assembly. Shaft 235 of drill guide 230 slides into handle 310 to make a connection. FIG. 5B shows assembled drill guide assembly 390, consisting of handle 310 and drill guide 23.

In a second embodiment, shown in FIG. 6, the orthopedic fixation system now includes an additional component. FIG. 6 shows fixation system 500 consisting of one or more implant kits 200, 201, and 202, instrument kit 300, and sizing guide 400. Implant kits 200, 201, and 202 and instrument kit 300 functions the same as in the preferred embodiment. Sizing guide 400 is shown in more detail in FIG. 7. It is a sterile packaged device made from plastic or a similar disposable material, with incremental projections on the perimeter. Representative projections 410 and 411 are shown in FIG. 7, however, any number of projections could be situated on the perimeter. Projections 410 and 411 have a known separation distance corresponds to the previously described separation distance of legs 206 and 207 on implant 205. The measurement 415 between projections 410 and 411 is shown on sizing guide 400.

Figure 8D:
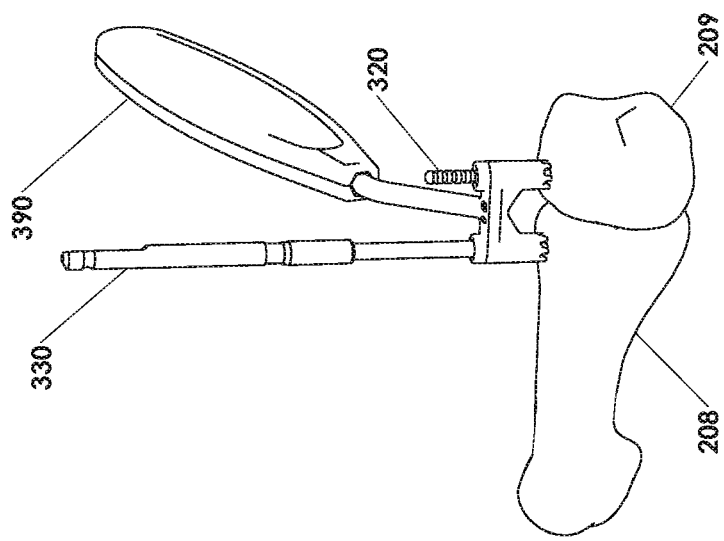
Figure 8C:
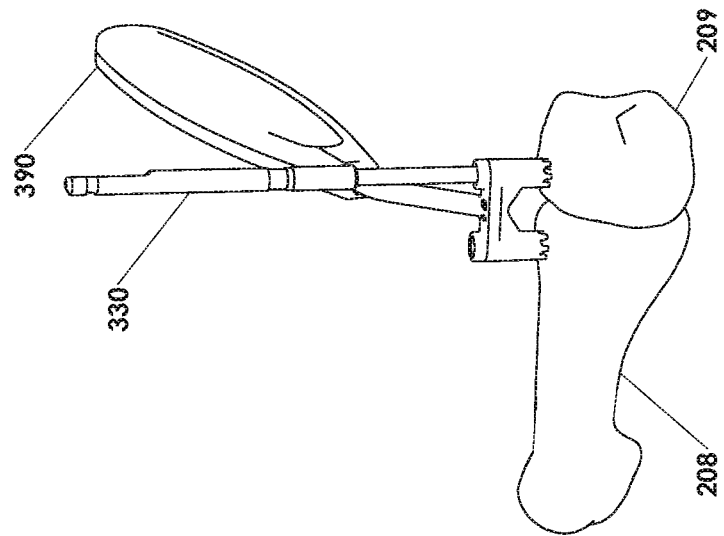
Figure 9:
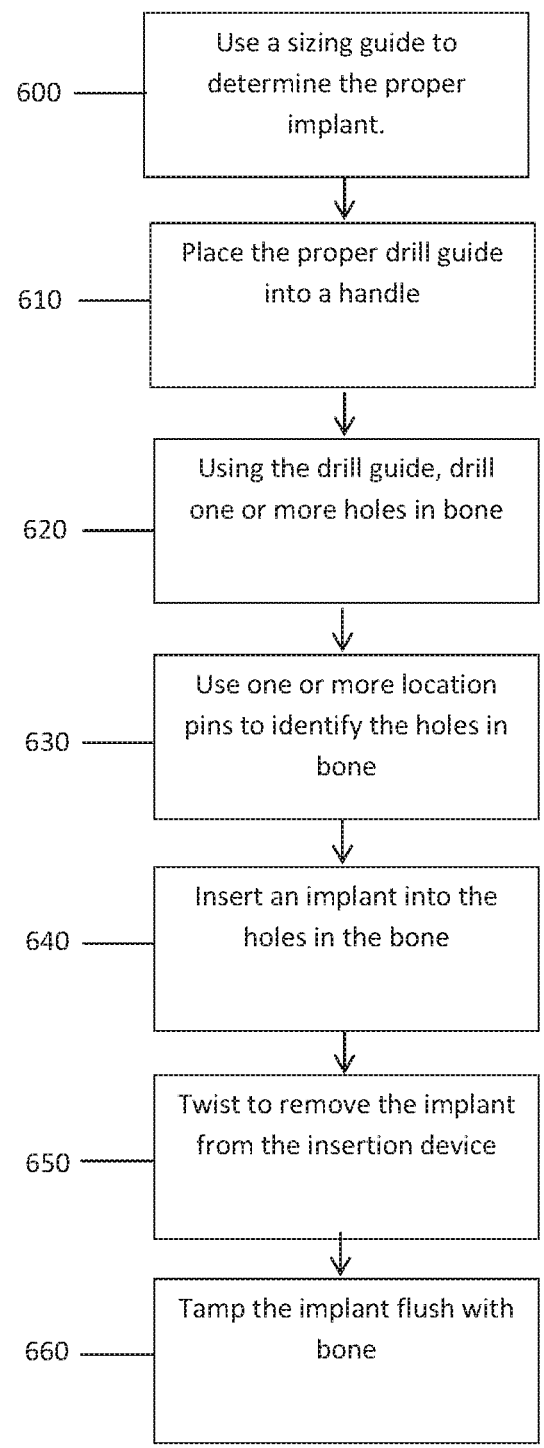
FIG. 9 provides a method for using a sterile orthopedic fixation system.

FIGS. 8A-8J show a sequence of images illustrating the use of a sterile-packaged orthopedic fixation system. FIG. 9 shows a method for using a sterile orthopedic fixation system that corresponds to FIGS. 8A-8J. FIG. 8A and step 600 of FIG. 9 show sizing guide 400 being used to determine the proper size of implant needed for bones 208 and 209. FIG. 8B and step 610 of FIG. 9 show drill guide assembly 390 being created from handle 310 and drill guide 230 by inserting shaft 235 into handle 310. FIG. 8C and step 620 of FIG. 9 show drill guide assembly 390 and drill bit 330 being used to drill a hole into bone 209. FIG. 8D shows locating pin 320 positioned in drill guide assembly 390 and extending into the hole in bone 209. Locating pin 320 secures the drill guide assembly 390 in place while drill bit 330 is used to drill a hole in bone 208. FIG. 8E and step 630 of FIG. 9 show drill guide assembly 390 with two locating pins 320 securing it to bone. FIG. 8F shows that the two locating pins 320 are left in bones 208 and 209. FIG. 8G and step 640 of FIG. 9 show implant 205 mounted to insertion device 220, being positioned over bones 208 and 209. FIG. 8H and step 650 of FIG. 9 show insertion device 220 being twisted off implant 205 to release implant 205 into bones 208 and 209. FIG. 8I and step 660 of FIG. 9 show implant 205 being pressed flush against bones 208 and 209 by tamp 340. Finally, FIG. 8J shows multiple implants 205 in position on bones 208 and 209.

Figure 10:
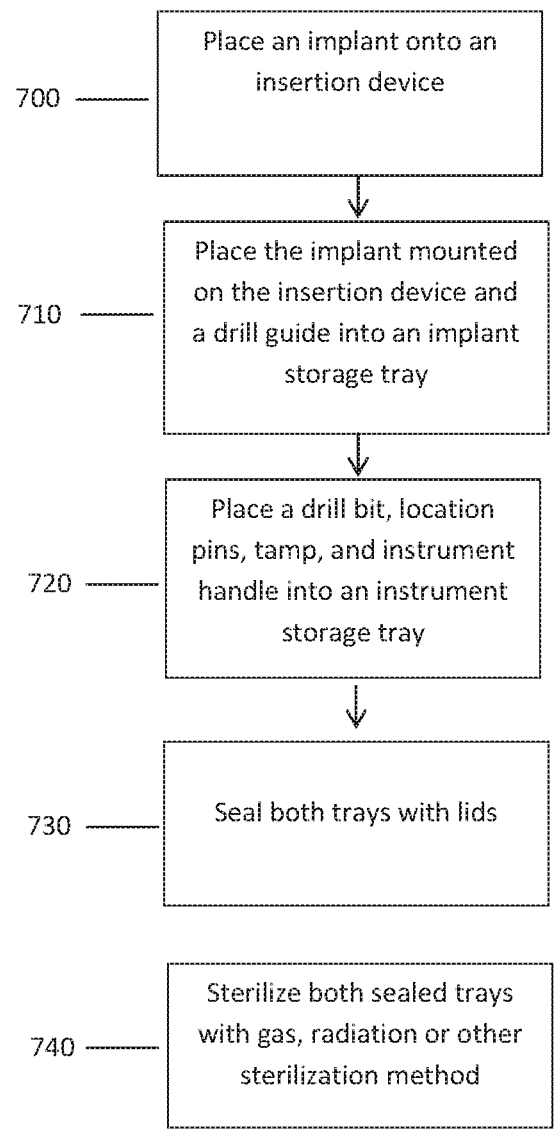
FIG. 10 provides a method for packaging a sterile orthopedic fixation system.

FIG. 10 shows a method for packaging a sterile orthopedic fixation system. Step 700 involves inserting the implant into an insertion device. In step 710, the insertion device with implant and corresponding drill guide is placed into a storage tray. In step 720, the components of an instrument kit, including drill bit, location pins, tamp, and instrument handle are placed into an instrument tray. In step 730 both trays are sealed with lids. Finally, in step 740 both trays are sterilized via gas, radiation or other sterilization method.

Figure 11:
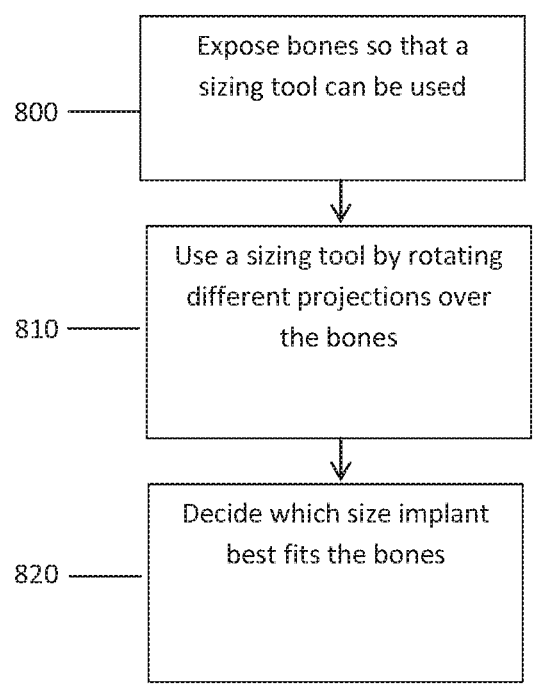
FIG. 11 provides a method for using an orthopedic sizing guide to select the proper implant.

FIG. 11 shows a method for using a sizing guide to determine the appropriate implant size for an orthopedic surgical procedure. Step 800 describes exposing bones that require surgery. Step 810 describes using a sizing tool by rotating it's projections over the bones. Step 820 involves selecting the proper implant that best fits the bones.

Although the present invention has been described in terms of the foregoing embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

We claim:

1. An orthopedic fixation system, comprising:
  a first shape memory implant, comprising a first leg and a second leg movable between an implanted position and an insertion position;
  a first implant insertion device adapted to engage the first shape memory implant and hold the first leg and the second legs in their insertion position;
  a first drill guide adapted for a drilling of holes into a first bone and a second bone whereby the first drill guide includes a fixed separation distance substantially equal to a distance between the first leg and the second leg of the first shape memory implant in their insertion position;
  a first package adapted to receive therein the first shape memory implant, the first implant insertion device, and the first drill guide;
  a second shape memory implant, comprising a first leg and a second leg movable between an implanted position and an insertion position;
  a second implant insertion device adapted to engage the second shape memory implant and hold the first leg and the second legs in their insertion position;
  a second drill guide adapted for a drilling of holes into a first bone and a second bone whereby the second drill guide includes a fixed separation distance substantially equal to a distance between the first leg and the second leg of the second implant in their insertion position;
  a second package adapted to receive therein the second shape memory implant, the second implant insertion device, and the second drill guide; and
  a sizing device, comprising first projections defining therebetween a first fixed distance and second projections defining therebetween a second fixed distance, wherein:
    the first fixed distance is different than the second fixed distance,
    the first fixed distance is substantially equal to the distance between the first leg and the second leg of the first shape memory implant in their insertion position, and
    the second fixed distance is substantially equal to the distance between the first leg and the second leg of the second shape memory implant in their insertion position.

2. The orthopedic fixation system according to claim 1, wherein the sizing device is adapted for placement of one of the first projections and the second projections across the first bone and the second bone to determine which of the first shape memory implant with its first and second legs in their insertion position and the second shape memory implant with its first and second legs in their insertion position is a proper size for fusion of the first and second bones.

3. The orthopedic fixation system according to claim 1, comprising a drill bit, locating pins, and tamp adapted for use during an insertion of one of the first shape memory implant and the second shape memory implant.

4. An orthopedic fixation system, comprising:
a first shape memory implant, comprising a first leg and a second leg movable between an implanted position and an insertion position;
a first implant insertion device adapted to engage the first shape memory implant and hold the first leg and the second legs in their insertion position;
a first drill guide adapted for a drilling of holes into a first bone and a second bone whereby the first drill guide includes a fixed separation distance substantially equal to a distance between the first leg and the second leg of the first shape memory implant in their insertion position;
a first package adapted to receive therein the first shape memory implant, the first implant insertion device, and the first drill guide;
a second shape memory implant, comprising a first leg and a second leg movable between an implanted position and an insertion position;
a second implant insertion device adapted to engage the second shape memory implant and hold the first leg and the second legs in their insertion position;
a second drill guide adapted for a drilling of holes into a first bone and a second bone whereby the second drill guide includes a fixed separation distance substantially equal to a distance between the first leg and the second leg of the second implant in their insertion position;
a second package adapted to receive therein the second shape memory implant, the second implant insertion device, and the second drill guide; and
a sizing device, comprising first projections defining therebetween a first fixed distance and second projections defining therebetween a second fixed distance, wherein:
the first fixed distance is different than the second fixed distance,
the first fixed distance is substantially equal to the fixed separation distance of the first drill guide, and
the second fixed distance is substantially equal to the fixed separation distance of the second drill guide.

5. The orthopedic fixation system according to claim 4, wherein the sizing device is adapted for placement of one of the first projections and the second projections across the first bone and the second bone to determine which of the first shape memory implant with its first and second legs in their insertion position and the second shape memory implant with its first and second legs in their insertion position is a proper size for fusion of the first and second bones.

6. The orthopedic fixation system according to claim 4, comprising a drill bit, locating pins, and tamp adapted for use during an insertion of one of the first shape memory implant and the second shape memory implant.

7. An orthopedic fixation system, comprising:
a first shape memory implant, comprising a first leg and a second leg movable between an implanted position and an insertion position;
a first implant insertion device adapted to engage the first shape memory implant and hold the first leg and the second legs in their insertion position;
a first drill guide adapted for the drilling of holes into a first bone and a second bone whereby the first drill guide includes a fixed separation distance substantially equal to a distance between the first leg and the second leg of the first shape memory implant in their insertion position;
a second shape memory implant, comprising a first leg and a second leg movable between an implanted position and an insertion position;
a second implant insertion device adapted to engage the second shape memory implant and hold the first leg and the second legs in their insertion position;
a second drill guide adapted for the drilling of holes into a first bone and a second bone whereby the second drill guide includes a fixed separation distance substantially equal to a distance between the first leg and the second leg of the second implant in their insertion position; and
a sizing device, comprising first projections defining therebetween a first fixed distance and second projections defining therebetween a second fixed distance, wherein:
the first fixed distance is different than the second fixed distance,
the first fixed distance is substantially equal to the distance between the first leg and the second leg of the first shape memory implant in their insertion position, and
the second fixed distance is substantially equal to the distance between the first leg and the second leg of the second shape memory implant in their insertion position.

8. The orthopedic fixation system according to claim 7, wherein the sizing device is adapted for placement of one of the first projections and the second projections across the first bone and the second bone to determine which of the first shape memory implant with its first and second legs in their insertion position and the second shape memory implant with its first and second legs in their insertion position is a proper size for fusion of the first and second bones.

9. The orthopedic fixation system according to claim 7, wherein:
the first fixed distance of the sizing device is substantially equal to the fixed separation distance of the first drill guide; and
the second fixed distance of the sizing device is substantially equal to the fixed separation distance of the second drill guide.

10. The orthopedic fixation system according to claim 9, wherein the sizing device is adapted for placement of the first projections and the second projections across the first bone and the second bone to determine which of the first shape memory implant with its first and second legs in their insertion position and the second shape memory implant with its first and second legs in their insertion position is a proper size for fusion of the first and second bones.

11. The orthopedic fixation system according to claim 7, comprising a drill bit, locating pins, and tamp adapted for use during an insertion of one of the first shape memory implant and the second shape memory implant.

12. The orthopedic fixation system according to claim 7, comprising:
a first package adapted to receive therein the first shape memory implant, the first implant insertion device, and the first drill guide;
a second package adapted to receive therein the second shape memory implant, the second implant insertion device, and the second drill guide.

* * * * *